(12) United States Patent
Birch et al.

(10) Patent No.: US 8,617,907 B2
(45) Date of Patent: Dec. 31, 2013

(54) DETERMINING THE PRESENCE OR AMOUNT OF A METAL-LABELLED SPECIES

(75) Inventors: Brian Jeffrey Birch, Higham Ferrers (GB); Camilla Sofia Forssten, London (GB); Alena Kabil, London (GB); Robert Andrew Porter, Rushden (GB)

(73) Assignee: Alere Switzerland GmbH (CH)

( * ) Notice: Subject to any disclaimer, the term of this patent is extended or adjusted under 35 U.S.C. 154(b) by 583 days.

(21) Appl. No.: 11/570,174

(22) PCT Filed: Jun. 7, 2005

(86) PCT No.: PCT/GB2005/002248
§ 371 (c)(1),
(2), (4) Date: Sep. 15, 2008

(87) PCT Pub. No.: WO2005/121792
PCT Pub. Date: Dec. 22, 2005

(65) Prior Publication Data
US 2009/0098662 A1    Apr. 16, 2009

Related U.S. Application Data

(60) Provisional application No. 60/584,271, filed on Jun. 30, 2004.

(30) Foreign Application Priority Data

Jun. 7, 2004   (GB) .................................. 0412659.5

(51) Int. Cl.
*G01N 33/553*    (2006.01)

(52) U.S. Cl.
USPC ........ 436/525; 436/518; 436/524; 435/283.1; 435/7.1; 435/287.1; 435/287.2; 205/792; 205/794.5

(58) Field of Classification Search
USPC ................ 436/518, 524, 525; 435/283.1, 7.1, 435/287.1, 287.2; 205/792, 794.5
See application file for complete search history.

(56) References Cited

U.S. PATENT DOCUMENTS

| | | | |
|---|---|---|---|
| 6,096,474 A * | 8/2000 | Jonckheere | 430/204 |
| 6,808,939 B2 * | 10/2004 | Sigal et al. | 436/546 |
| 7,045,364 B2 * | 5/2006 | Limoges et al. | 436/525 |
| 2006/0019319 A1 * | 1/2006 | Billadeau et al. | 435/7.21 |

FOREIGN PATENT DOCUMENTS

WO    02/01178    *  1/2002

* cited by examiner

*Primary Examiner* — Melanie Y Brown
(74) *Attorney, Agent, or Firm* — Foley Hoag LLP

(57) ABSTRACT

A method for determining the presence or amount of a metal-labelled species in a sample may include causing the metal of the metal-labelled species in the sample to form a soluble electrochemically-active complex which is stable relative to moieties present or potentially present in the sample which will form an insoluble and/or electrochemically-inactive complex with the metal, and electrochemically measuring the formed complex to provide an indication of the presence or amount of the metal-labelled species.

6 Claims, 5 Drawing Sheets

Filter paper sink
Immunofilter

DETERMINING THE PRESENCE OR AMOUNT OF A METAL-LABELLED SPECIES

CROSS-REFERENCE TO RELATED APPLICATIONS

This application is the National Stage of International Application No. PCT/GB2005/002248, filed Jun. 7, 2005, which claims the benefit of U.S. Provisional Application No. 60/584,271, filed Jun. 30, 2004, and also claims the right of priority to GB Application No. 0412659.5, filed Jun. 7, 2004. Each of these applications is hereby incorporated herein by this reference.

FIELD

The present disclosure relates to methods and devices for determining the presence or amount of a metal-labelled species. In particular, but not exclusively, it relates to methods and devices for the detection of such species which comprise or are specifically attached to an analyte of interest.

BACKGROUND

Specific binding species, such as antibodies, that are conjugated to a label are routinely employed as reagents for rapid assays in the detection of analytes. One such assay is described in EP0291194A1, incorporated herein by reference. In this assay, a lateral flow porous carrier is provided with a mobilisable particulate-labelled antibody specific to the analyte of interest. It is further provided with a second antibody which is also specific for the analyte but which is immobilised in a detection zone. Analyte binds with the labelled mobilisable antibody to form a first complex which is subsequently captured by the second immobilised antibody in the detection zone. The extent of label present in the detection zone provides an indication of the amount of analyte present in a sample. The label may be a particulate species such as gold and its presence in the detection zone may be detected either visually or optically.

Another method for the detection of a labelled specific binding species is disclosed in U.S. Patent Application Publication No. US2003/0186274-A1, incorporated herein by reference. In this method, the extent or presence of a metal-labelled binding species is detected by dissolving the label in the presence of an oxidising agent, such as a strong acid, to form metal ions. The ions are then deposited onto an electrode surface by electrochemical reduction in the presence of a suitably negative potential. The potential is then varied to reoxidise the metal which then returns to solution, producing a current response. The intensity of this response provides an indication of the amount of metal ions deposited at the electrode surface and hence the amount of label initially present. This type of electroanalytical technique is known as stripping voltammetry and can be used for the measurement of low amounts of metal ions (e.g. parts per million or less). The method may be used to detect the presence or extent of any analyte having a binding specificity for the labelled binding species.

The method of US2003/0186274-A1 is exemplified using gold as the label. However, silver can in many ways be considered to be a better label for use in electrochemical detection, mainly because it is easier to oxidise silver to form silver ions than it is gold. For example, the oxidising agents required for the formation of silver ions from silver are less powerful than those required for forming gold ions from gold and hence more appropriate for use in diagnostic kits.

Although silver is disclosed in US2003/0186274-A1 as a metal particle which can be detected, the methods described therein cannot be used for the electrochemical detection of silver and similar metals in biological samples. This is because the oxidised forms of these metals will react with species found in biological samples, such as blood, plasma and urine, to form insoluble electrochemically-inactive complexes. For example, the concentration of chloride ions in urine is typically 150 mM and therefore any silver ions formed by oxidation will immediately precipitate as AgCl and will thus be prevented from being oxidised at the electrode surface. Similarly, bromide ions and sulphur-containing species such as cysteine also present in biological samples will form insoluble electrochemically-inactive complexes with silver ions.

SUMMARY

A method for determining the presence or amount of a metal-labelled species in a sample may include causing the metal of the metal-labelled species in the sample to form a soluble electrochemically-active complex which is stable relative to moieties present or potentially present in the sample which will form an insoluble and/or electrochemically-inactive complex with the metal, and electrochemically measuring the formed complex to provide an indication of the presence or amount of the metal-labelled species.

A method for determining the presence or amount of an analyte in a sample may include contacting the sample suspected of containing the analyte with a metal-labelled binding partner to form a metal labelled species, oxidising the metal-labelled species and causing the resulting metal ion to form a soluble electrochemically-active complex which is stable relative to moieties present or potentially present in the sample which are able to form an insoluble and/or electrochemically-inactive complex with the metal ion, and electrochemically measuring the formed soluble electrochemically-active complex to provide an indication of the presence or amount of analyte.

A kit may include (a) a metal-labelled binding partner capable of binding an analyte suspected of being present in a sample to form a metal-labelled species, (b) one or more reagents for causing the metal of the metal-labelled species to form a soluble electrochemically-active complex which is stable relative to moieties present or potentially in the sample which will form an insoluble and/or electrochemically-inactive complex with the metal, (c) a volume in which the metal-labelled binding partner can bind the analyte, and/or (d) a capture zone for immobilising the metal-labelled species so that the one or more reagents can cause formation of the soluble electrochemically-active complex.

DETAILED DESCRIPTION

Methods

In certain embodiments, electrochemical measurement of the metal takes place via the formation of a soluble electrochemically-active complex of the metal. In this way, the metal is prevented from reacting with agents or moieties in the sample which would otherwise result in the formation of insoluble and/or electrochemically-inactive complexes. Thus, electrochemical measurement of the formed complex may be carried out conveniently and easily without the need for removal of such moieties that would otherwise render the metal unavailable for electrochemical measurement. Although US2003/0186274-A1 discloses that the metal ions produced in the method disclosed therein may be complexed, the purpose of this is described as being to transform a non-electroactive metal ion into a detectable electroactive compound and to form a more hydrophobic moiety which can adsorb to the electrode. This is in contrast to certain embodiments of the present subject matter, in which an electroactive metal ion is transformed into a complex to prevent it from forming an insoluble and/or electrochemically-inactive complex with moieties present in the sample.

In one embodiment, the electrochemically-active complex is formed by oxidising the metal and then reacting the metal ion formed with a suitable complexing agent. This may be achieved by oxidising the metal in the presence of a suitable complexing agent.

The metal label used may be silver, although other metals may be used such as lead, cadmium, copper, thallium, mercury and zinc. Compared to gold, the conventional and favoured particulate metal of choice, silver forms easily measurable electrochemical responses on platinum or carbon electrodes. This allows the use of carbon electrodes, which may be conveniently and inexpensively prepared.

The or each oxidising reagent, when used, in combination with the carbon electrode, when present, serves to provide a stable reference potential against which the potential may be referenced. This avoids the need to construct a separate electrode, such as for example a silver/silver chloride electrode as is commonly used.

In one embodiment, the metal label is a particulate label, such as a silver sol. The advantage of providing a particulate label is that a single label may be oxidised to provide a very large number of metal ions, e.g. $10^6$ or more depending upon the size of the sol, and therefore provides greater sensitivity. Metal sols are commercially-available and may be conjugated to binding reagents by known methods such as described by EP0291194A1.

The use of silver is also more convenient than gold as it requires less harsh oxidising conditions to form silver ions than more noble metals such as gold. For example, oxidation of metallic gold to ionic gold ($AuCl_4$) requires a mixture of concentrated nitric acid plus concentrated hydrochloric acid, or sodium hypochlorite and hydrochloric acids. By way of contrast, to oxidise silver particles to silver ions, peroxides, ferric ions and ferricyanide can be used as oxidants. The oxidation may also be carried out at a more favourable pH, for example between 3 and 7.

The metal label may be formed into an electrochemically-active complex which can be detected electrochemically. As used herein, an "electrochemically-active" species is an ion, neutral compound or complex which can undergo the gain or loss of one or more electrons.

The function of the electrochemically-active complex is to prevent the metal from reacting with species in the sample which result in insoluble and/or electrochemically-inactive complexes which cannot be detected electrochemically. For example, silver ions will react with halides, such as chloride, to form an insoluble salt or with sulphur-containing species such as cysteine, glutathione, cysteinylglycine and other sulph-hydryl compounds to form silver ion complexes that are electrochemically inactive. Accordingly, the electrochemically-active complex must be stable in the presence of such species. It will be appreciated by those skilled in the art that the electrochemically-active complex will be in dynamic equilibrium with the metal (or metal ions) and the complexing species. The metal or metal ions will also be in equilibrium with moieties present in the sample which are able to form electrochemically-inactive and/or insoluble complexes. Thus, in principle, all of the above species will be present to some extent. However, the position of these equilibria will depend at least in part upon the amounts of complexing species present which are able to form soluble electrochemically-active complex, the amount of species present in the sample which are capable of forming insoluble and/or electrochemically-inactive complexes with the metal or metal ions and the amount of metal or metal ions present. Thus, the term stable is intended to refer to the situation where the electrochemically-active complex is formed preferentially and wherein the levels of electrochemically inactive and/or insoluble complexes present are negligible with respect to the levels of electrochemically-active complexes. The level of electrochemically-inactive and/or insoluble complex present may have an insignificant effect upon the measurement result. The greater the amount of complexing species initially present, the more the equilibrium will be shifted towards the formation of the soluble electrochemically-active complex and therefore lower amounts of metal or metal ions will be present. For this reason, the complexing species is provided in excess to ensure the preferential formation of electrochemically active complex, irrespective of the levels of moieties present in the sample which are capable of forming insoluble and/or electrochemically-inactive complexes with the metal.

The disclosed methods, devices, and kits may be suitable for use with biological samples, including all liquids that can be obtained from a mammalian body, including, for example, blood, plasma, urine, lymph, gastric juices, bile, serum, saliva, sweat, and spinal and brain fluids. Furthermore, the bodily liquids may be either processed (e.g., serum) or unprocessed. Methods of obtaining a sample from a subject are known to those skilled in the art. The biological sample may be obtained from a solid sample, e.g. tissue, that has been treated in order to provide a liquid sample. The disclosed methods, devices, and kits may also be suitable for measurement in other liquids, including industrial or environmental liquids, such as waste-water or sea-water that might contain high amounts of species that are capable of forming insoluble and/or electrochemically-inactive complexes with the metal. The sample may be of plant origin. Where the sample to be tested contains protein moieties, iodoacetamide may be added to react with thiols found in proteins to form thioesters. This prevents metal ions reacting with proteins through thiol groups and becoming unable to form the soluble electrochemically-active complex.

As mentioned, the electrochemically-active complex may be formed by oxidising the metal and then reacting the metal ion formed with a suitable complexing agent. Any convenient oxidant which is capable of oxidising the metal may be used, such as permanganate, chromate, peroxides, persulphates, ferric ions and ferricyanide. In one specific embodiment, the oxidant is ferric ions as it is a particularly mild oxidation agent. In accordance with the present disclosure, the oxidant may be provided in a reduced form and only oxidised to its active form when required. Such oxidation may be chemical or electrochemical. In certain embodiments, oxidation may be induced by contact of the reduced-form oxidant with a sample to be tested.

In one embodiment, silver is oxidised using iron in the +III oxidation state according to the following reaction scheme:

$$Fe^{3+} + Ag \rightarrow Ag^+ + Fe^{2+}$$

Iron in the +III oxidation state may be provided in the form of a suitable soluble ferric salt such as nitrate, acetate, citrate, ferric ammonium sulphate.

As an alternative to ferric nitrate, potassium ferricyanide may be used as the oxidant according to the following reaction scheme, followed by reaction with thiocyanate or thiosulphate:

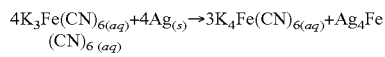

Ferricyanide (FeIII) may be generated by the oxidation of ferrocyanide (FeII) at the electrode for oxidising the metal, such as silver sol particles. There are several advantages to this approach. Firstly, ferricyanide can be generated in a controlled way and in controlled amounts at the point of use and at the time at which it is needed. This minimises any possible loss of metal by diffusion out of the measurement zone. The same electrode(s) may be employed for generating the oxidant as well as for determining the levels of metal ions. Secondly, ferrocyanide is more stable than ferricyanide in a dry form and therefore can be stored in a device or kit as disclosed herein until a sample is added. Thirdly, ferrocyanide forms weaker complexes with silver than ferricyanide, so it is a benefit only to generate the ferricyanide when needed.

The fact that ferrocyanide is relatively unreactive with silver and only becomes reactive upon oxidation is important in those embodiments of the disclosed methods, devices, and kits which involve the use of a silver-labelled binding partner to bind an analyte and thereby form the silver-labelled species (see below). In these embodiments, any unbound silver-labelled binding partner can be allowed to contact the ferrocyanide, without the risk of the unbound silver-labelled binding partner distorting results by providing silver ions which form the soluble electrochemically-active complex. After any unbound silver-labelled binding partner has been removed, ferrocyanide may be oxidised to form ferricyanide so that only the silver of the bound silver-labelled species forms the soluble electrochemically-active complex.

This makes far easier the provision of a one-step test/kit wherein the necessary reagents are provided in the dry state within a device and wherein the user only needs to apply a liquid sample in order to conduct the test. In such a test/kit, the sample would itself act as the washing fluid, removing any unbound silver-labelled binding partner from the zone/area at which the soluble electrochemically-active complex is detected. Ferrocyanide may be provided upstream or at the detection zone. Potassium ferrocyanide may be used as it is highly water soluble, relatively unreactive with Ag and stable in the dry state.

After formation of the silver ion, excess ammonium thiocyanate may be used to form a soluble silver ion complex which can be detected electrochemically, as follows:

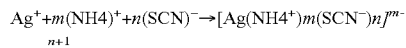

Excess ammonium thiosulphate may be used in place of thiocyanate in order to form the soluble silver ion complex. The silver ion complex is formed preferentially with respect to the insoluble silver salt and therefore remains in the form of the soluble complex even in the presence of those species which are able to form insoluble salts with silver ions.

The reagents which are used to oxidise the silver (or other metal) and form the stable complex may exist in the dry state, which makes their incorporation into an immunoassay device convenient. During use, the reagents can be dissolved by the biological sample to be analysed.

A further advantage of using silver as the metal label is that the reduction potential of the silver species stripped from the electrode occurs at a lower negative potential compared to that of silver ions. This reduces interference and background effects from electrochemically active compounds such as ascorbate and other metal ions such as copper, cadmium and mercury that may be present.

Measurement of the electrochemically-active complex may be carried out by any convenient electrochemical method. Anodic stripping voltammetry (or polarography) with a potential scan which may be linear, cyclic, square-wave, normal pulse or differential pulse, or with a superimposed sinusoidal voltage, may be used. Alternatively, anodic stripping chronopotentiometry may be used. Other techniques may be used, such as ion exchange voltammetry, adsorptive cathodic stripping voltammetry (or polarography) with a scan which may be linear, cyclic, square-wave, normal pulse or differential pulse, or with a superimposed sinusoidal voltage, or chronoamperometry, chronocoulometry or linear, cyclic, square-wave, normal pulse or differential pulse voltammetry (or polarography) or voltammetry (or polarography) with a superimposed sinusoidal voltage.

The metal-labelled species may be formed by the binding of an analyte to be detected with a metal-labelled binding partner. Thus, the metal-labelled species, and hence the soluble electrochemically-active complex formed from the metal-labelled species, are indicators of the presence or amount of the analyte in the biological sample. The metal-labelled binding partner may be anything capable of binding to the analyte to be detected. Thus, depending on the analyte to be detected, it may be an antibody or antigen binding fragment thereof, a protein receptor, a T cell receptor, an antigen, a hapten, a protein, a peptide, an oligonucleotide, a boronic acid derivative, polymeric acid or base, carbohydrate, lectin, complimentary nucleotide or peptide sequence, specific protein binder, a nucleic acid (such as DNA or RNA), analyte conjugate and the like.

The term "antibody" as used herein refers to immunoglobulin molecules and immunologically active portions or fragments of immunoglobulin molecules, i.e., molecules that contain an antigen binding site that specifically binds an antigen. The immunoglobulin molecules useful in the disclosed methods, devices, and kits can be of any class (e.g., IgG, IgE, IgM, IgD and IgA) or subclass of immunoglobulin molecule. Antibodies includes, but are not limited to, polyclonal, monoclonal, bispecific, humanised and chimeric antibodies, single chain antibodies, Fab fragments and F(ab')$_2$ fragments, fragments produced by a Fab expression library, anti-idiotypic (anti-Id) antibodies, and epitope-binding fragments of any of the above. An antibody, or generally any molecule, "binds specifically" to an antigen (or other molecule) if the antibody binds preferentially to the antigen, and, e.g., has less than about 30%, preferably 20%, 10%, or 1% cross-reactivity with another molecule. Portions of antibodies include Fv and Fv' portions.

The analyte to be detected may be measured using an immunoassay. Such assays may be competitive or non-competitive (sandwich) immunoassays. Such assays, both homogeneous and heterogeneous, are well-known in the art.

In one embodiment, an immunoassay is performed by contacting a sample from a subject to be tested with an appropriate metal-labelled antibody to form a metal-labelled species, followed by treatment of the species in order to form the electrochemically active complex (which may be oxidation of the metal and complexation of the resulting metal ion), followed by electrochemical measurement of the electrochemically active complex in order to determine the amount or presence thereof, which corresponds to the amount or presence of analyte.

An analyte can be detected in a biological sample by means of a two-step sandwich assay. In the first step, a capture reagent (e.g., an anti-analyte antibody) is used to capture the analyte. The capture reagent can optionally be immobilised on a solid phase. In the second step, a metal-labelled detection reagent is used to detect the captured analyte. Alternatively, the capture reagent may be labelled with the metal, and the detection reagent may be immobilised. This allows detection of the analyte in a specific area where the detection reagent is immobilised.

In one embodiment, a lateral flow immunoassay device may be used in the "sandwich" format wherein the presence of sufficient analyte marker in a sample will cause the formation of a "sandwich" interaction at the capture zone in the lateral flow assay. The capture zone as used herein may contain capture reagents such as antibody molecules, antigens, nucleic acids, lectins, and enzymes suitable for capturing the analyte to be detected. Other assays that may be used in the disclosed methods include, but are not limited to, flow-through devices.

Kits

A kit may be provided in combination with a reader device, which is for electrochemical measurement of the soluble electrochemically-active complex. In one embodiment, the kit is disposable and the reader reusable, the respective parts having to be engaged or otherwise associated together before use. Alternatively, they may be provided as a unitary system.

The kit or the reader may be provided with at least two electrodes for the electrochemical measurement. When provided in the kit, the electrodes may be able to be connected via terminals to electrode terminals present within or on an exterior surface of the reader. When provided in the reader, the kit is arranged such that the electrodes are located at a suitable location in the kit when the kit and reader are engaged together.

The reader may comprise signal transduction and signal processing means which serve to provide signals to the electrodes as well as to transduce and process the particular signals obtained from the electrodes. The reader may comprise display means for displaying information; means for receiving the kit, a power source or means to receive external power, memory means, calibration means, and optional data input/output means.

In one embodiment, the volume of the kit is formed by a multi-well plate or the like. The sample is placed in the well and the metal-labelled binding partner added. Any analyte present will then form the metal-labelled species. This species can be immobilised in a capture zone (e.g. a filter or immobilised antibody) so that the one or more reagents for causing the metal of the metal-labelled species to form a soluble electrochemically-active complex can be added thereto. Alternatively, the volume may be formed or provided by a porous carrier, which may be lateral-flow porous carrier, or a microfluidic device.

Where the disclosed methods, devices, and kits involve the formation of metal ions which are then complexed, in order to provide accurate results, the electrochemical measurement should be confined only to those metal ions which are complexed. That is to say, uncomplexed metal-labelled binding partner should not be oxidised, or if it is, it should not be allowed to influence the result of the measurement. This may be achieved by first contacting the sample with the binding partner in order to form the immobilised metal-labelled binding partner-analyte complex, followed by washing to remove any unbound metal-labelled binding partner from the vicinity of the capture zone. The one or more reagents for causing the metal of the metal-labelled species to form a soluble electro-chemically-active complex thereafter may be contacted with the immobilised zone in order to form the electrochemically stable metal ion complex.

The electrodes may be provided by a number of methods including various printing methods such as screen-printing, ink-jet printing, offset lithographic printing, rotary printing and so on. Alternatively, the electrodes may be deposited by vacuum deposition or by sputtering. The electrodes may be provided on an internal surface of the substrate. In the case of a two electrode construct, one of the electrodes is the working electrode and the other acts as a counter/reference electrode. A third electrode may be provided which may act as a reference electrode. The same or further electrodes may be provided to indicate the presence of sample in the chamber and/or to ensure that the chamber has filled correctly. The electrodes may be part of a planar screen-printed 3-carbon electrode construct. This construct may be made by printing low temperature carbon patterns onto a substrate, and then overprinting these with a pattern of low temperature dielectric to define the electrodes and to mask other carbon areas from water. The substrate may be a polymer, although alumina could be used. Deposition of the electrode material and dielectric can be achieved by a variety of techniques, including screen printing.

In one embodiment, immobilisation or capture of a metal-labelled species (the binding partner-analyte complex) is achieved by use of a filter structure. In the absence of analyte, the metal-labelled binding partner will pass through the filter and, in the presence of analyte, formation of the resultant complex will cause it to become immobilised or trapped at the filter.

Preferred features of each disclosed method, device, and kit are as for each of the other aspects mutatis mutandis. The patent documents mentioned herein are incorporated to the fullest extent permitted by law.

EXAMPLES

Example 1

Electrochemical Measurement of Silver Sol in Serum

Figure 1:
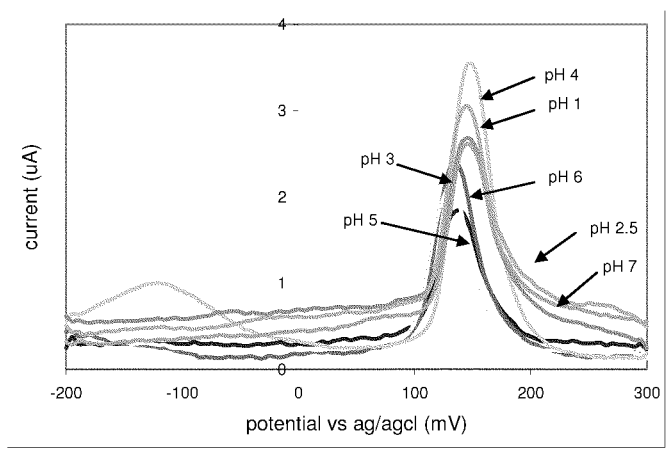
FIG. 1 is a graph of current vs. potential illustrating the optimum pH at which the silver ion complex is formed from silver when mixed with ammonium thiocyanate and ferric nitrate in aqueous solution.

Ammonium thiocyanate (0.4 g) was added to a 1 ml serum sample. As oxidant, ferric nitrate (0.01 g) in 1% EDTA (100 µl) was used with a pH 4 buffer (citric acid/sodium citrate). This pH had previously been found to give the optimum analytical signal for silver ions in both biological samples and pure buffers (see FIG. 1). From FIG. 1 it can be seen that pH4 is optimal as it provides the greatest current reading, i.e. sensitivity. It can also be seen that the oxidation reaction of the silver ion complex is pH dependent. However, when carrying out measurements in whole blood, a higher pH such as pH 7 may be chosen to avoid clotting of the blood sample. 10 µl of known concentrations of silver particles was added to the serum sample. These dissolved rapidly to give an optically clear solution.

Figure 2:
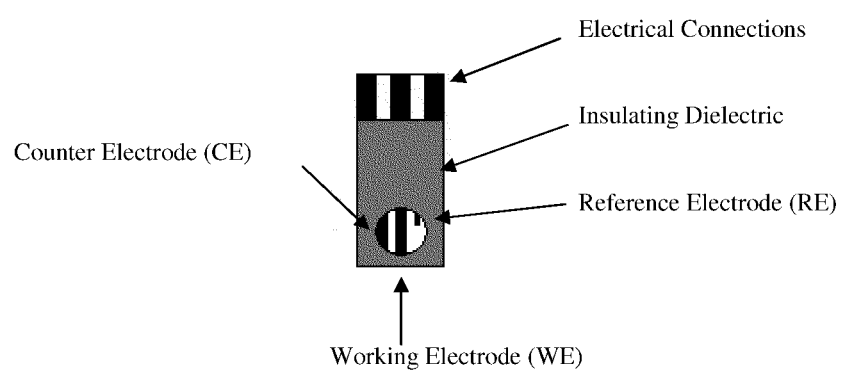
FIG. 2 is a schematic view of an electrode on which the electrochemical measurements according to the examples took place.

The measurements of the resultant silver ions were made on a planar screen-printed 3-carbon electrode construct (see FIG. 2). The electrode was made by printing low temperature carbon patterns (D2, Gwent Electronic Materials) onto 25µ alumina substrates. These were then overprinted with a pattern of low temperature dielectric (Gwent Electronic Materials) to define the electrodes and to mask other carbon areas from water (see FIG. 2).

The volume of sample applied in each case to the electrode surfaces was 10 ul. Carbon/ammonium thiocyanate/ferric ions was used as the reference electrode. This has a potential difference of approximately −450 mV vs Ag/AgCl/3.5M KCl half cell. The electroanalytical technique used was fast square wave anodic stripping voltammetry (FQWASV). Other standard electroanalytical techniques could however be employed.

Measurements were made using an Ezescan™ (Whistonbrook Technologies) operated in the stripping square voltammetric mode. Pre-concentration was carried out for 120 s at an accumulation potential (unstirred) of −900 mV. Stripping was initiated after this time (5 s resting period optional) between −900 mV and −100 mV with the instrument operating parameters: potential step 1mV; peak width 5 ms; half cycle amplitude 25 mV; frequency 100 Hz. The peak heights resulting from the scans were taken as indicative of silver ion concentration in the sample. Alternatively, the area defined by the peaks could be measured to provide an indication of the charge.

Figure 3:
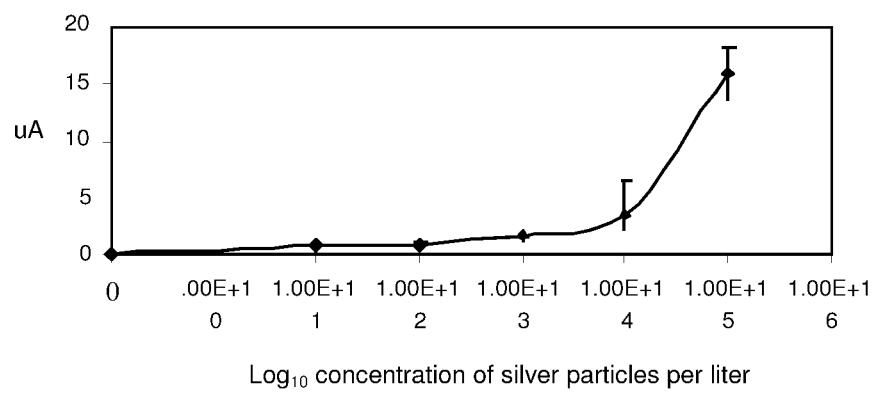
FIG. 3 is a graph showing the current response obtained for various amounts of silver particles present in the liquid sample according to the method of Example 1.
Figure 4:
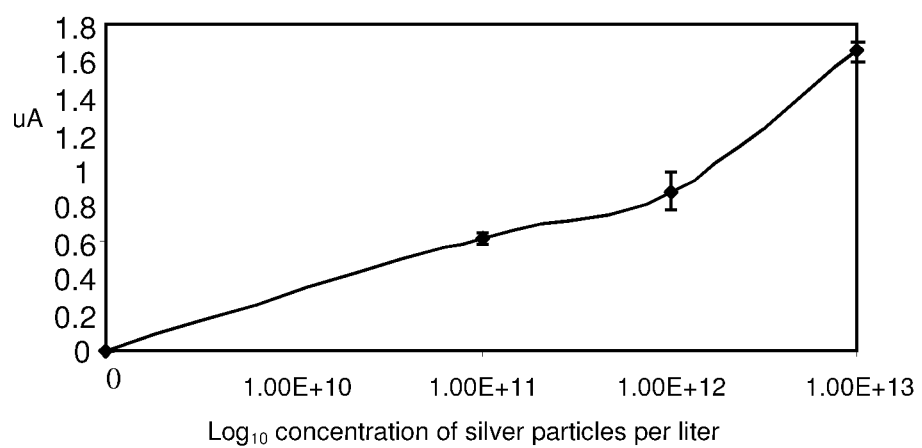
FIG. 4 is an expanded view of FIG. 3 obtained for a particular range of silver particle amount.

The results obtained are shown in FIGS. 3 and 4. It can be seen that the current response increases with increasing amounts of silver particles initially present.

Example 2

Determination of the Levels of hCG Analyte in Serum

Figure 5:
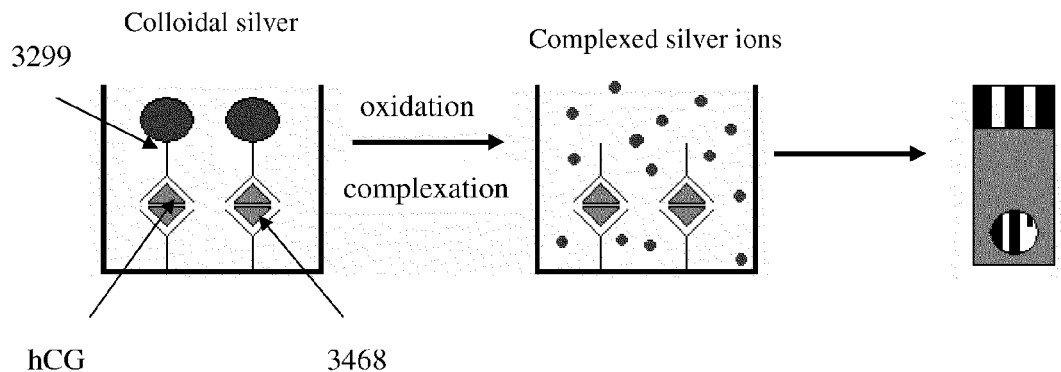
FIG. 5 is a schematic view of an immunoassay.

The electrochemical method of Example 1 was employed to determine the levels of the analyte human chorionic gonadotropin (hCG) in serum using a standard ELISA type procedure. In short, samples containing various levels of hCG analyte were mixed with silver particulate-labelled antibodies (anti-ahCG) to form a first antibody-analyte complex. This complex was then added to an ELISA plate comprising immobilised antibody reagent (anti-βhCG) to form a second immobilised antibody-analyte-antibody "sandwich" complex. Finally, excess unbound silver particulate-labelled first antibodies were removed from the plate by washing. This is shown schematically in FIG. 5.

Oxidation of the silver-antibody complex to form a soluble silver ion complex was subsequently carried out by addition of an aqueous sample containing the reagents described in Example 1, followed by the electrochemical measurement of the silver ions to provide a measurement of the amount of hCG analyte present.

The silver-labelled antibody reagent and the ELISA plate immobilised reagents were prepared according to standard procedures as follows.

S-acetylmercaptosuccinic acid (SAMSA) (Sigma) was reacted with anti-ahCG monoclonal antibodies (Mabs). A PD-10 size exclusion column (Pharmacia) was equlibrated with 25 ml of pH 6.0 phosphate buffer, 2.5 ml of MAb stock was loaded onto the column and eluted with 3.5 ml of pH 6.0 phosphate buffer. To 900 µl of phosphate buffer was added 100 µl of the eluted MAb solution and the absorbance was measured at 280 nm. The concentration was calculated (Abs=∈cl), ∈=1.4. The total mass of protein in solution was calculated (3.4 ml remaining). The moles of MAb was calculated (MW of MAb=150,000). The moles of SAMSA needed for 35 eq excess was calculated (MW of SAMSA=174.2). The amount of SAMSA in µl of SAMSA solution required given a SAMSA concentration of 50 mg/ml in dimethylformamide (DMF) was calculated.

SAMSA was dissolved in a dry DMF solution to a concentration of 50 mg/ml and the appropriate quantity of solution was added to the MAb solution while mixing. The resulting solution was incubated overnight with mixer at room temperature.

The conjugation of silver colloid with the resulting SAMSA-linked anti-ahCG monoclonal antibodies (MAb) was carried out according to the following steps.

A known amount of silver colloid was incubated with a non-ionic surfactant (Pluronic F108-PMPI) to reduce non specific binding. 5 mg of F108-PMPI in deionised water was added into an eppendorf tube and approximately 2 mg of silver sol was added. This was incubated for about 1 hour at room temperature on a rotary mixer. The solution was then centrifuged at 17000 rpm for 15 min at 5° C. The supernatant was removed and the pellet resuspended in 1 ml of 50 mM HEPES pH 7.5.

The SAMSA-MAb was deprotected to give monoclonal antibody thiols (MAb-SH) for more effective binding to silver colloid. To a 1 ml aliquot of SAMSA-MAb solution, 40 µl of 0.1M tris hydroxymethylaminoethane (Tris) solution was added and mixed for 5 min. 20 µl of 0.1M ethylenediaminetetraacetic acid (EDTA) solution was added and mixed for 5 min. 40 µl of 1M hydroxylamine solution was added and mixed for 5 min. NAP-10 column packing (Pharmacia) was equilibrated with 20 ml of pH 7.5 4-(2-hydroxyethyl)-1-piperazineethanesulfonic acid (HEPES), 1 ml of deprotected MAb solution was loaded and eluted with 1.5 ml of HEPES.

The silver colloid was then reacted with the deprotected SAMSA-Mab. The silver colloid suspension was divided into two aliquots and 500 µl of deprotected SAMSA Ab (MAb-SH) solution was added to each aliquot while mixing. The samples were incubated overnight and centrifuged at 17000 rpm for 30 min at 5° C., the supernatant removed and each sample was resuspended in 500 µl of borate buffer (pH 8.6). The samples were recombined into one eppendorf tube and centrifuged at 17000 rpm for 30 min at 5° C. The supernatant was discarded and the solid resuspended in 1 ml of borate buffer. The resulting silver particulate-labelled antibodies were stored at 4° C.

Monoclonal anti-βhCG antibody reagent was immobilised to an ELISA plate (Greiner high binding plates) as follows.

200 μl of anti-βhCG in 50 mM borate buffer, pH 8.6 was added to each well. The plate was covered and incubated with shaking at 37° C. for 1 hr followed by washing. DBS/BSA buffer (Dulbecco's Phosphate Buffered Saline—1 tablet per 100 ml R.O. water, 1% BSA) was added to the wells and left overnight. The buffer was then discarded. 200 μl of the desired concentration of hCG in DBS/BSA buffer (0, 0.2, 1, 5, 10, 20 and 50 mIU respectively) was added in duplicates to the wells and incubated at 37° C. for 1 hr followed by washing. 100 μl of excess silver colloid conjugated to SAMSA-MAb, in borate buffer (pH8.6) was added to each well and incubated at 37° C. for 1 hr followed by washing.

Figure 6:
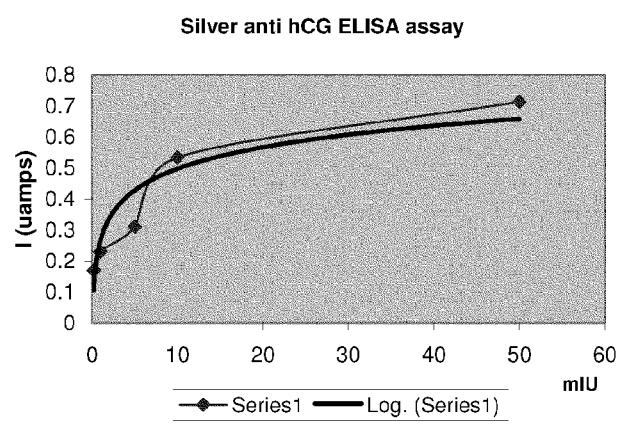
FIG. 6 is the current response obtained as a function of the levels of the analyte human chorionic gonadotropin (hCG) present in accordance with the method of Example 2.

Oxidation of the immobilised silver-antibody complex was carried out by addition of 100 μl of 5M ammonium thiocyanate, 0.05M Citrate buffer pH4, 1M Ferric nitrate, 1% EDTA solution to each well followed by incubation at 37° C. for 30 seconds. The solution was removed by pipette, placed onto the 3-electrode structure described in Example 1 and the amount of silver ions was then measured electrochemically as in Example 1 except that a conventional Ag/AgCl reference electrode was used. Hence the accumulation potential was −300 mV and the stripping potentials were varied between −300 mV and +400 mV. The results are shown in FIG. 6, from which it can be seen that increasing current responses were obtained with increasing levels of analyte.

Example 3

Figure 7:
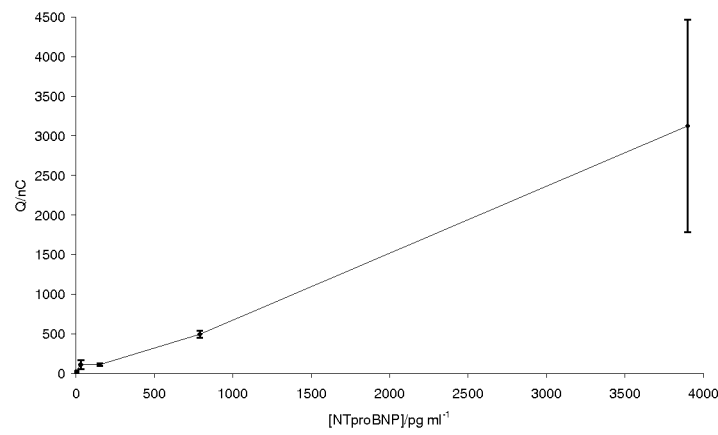
FIG. 7 is a graph showing measured charge vs. concentration of NTproBNP. Error bars represent one standard deviation in the measured signal based on 2 or 3 measurements.

NTproBNP Immunoassay Based on the Utilisation of Magnetic Capture Particles and Silver Sol Signal Particles In this example, an anti NT-proBNP antibody labelled with Ag and an anti NT-proBNP antibody labelled with latex coated magnetic particles were mixed with NT-proBNP to form a sandwich complex. The resulting sample was concentrated under a magnetic field which had the effect of separating the unbound Ag-labelled antibody from the complex (as well as any unbound magnetic particle labelled antibody). The supernatant was removed. The sample was resuspended in PBS and provided on an electrode surface. Ferrocyanide was added to the electrode surface and oxidised to provide the active reagent, ferricyanide. The amount of Ag ions produced was measured by reduction onto an electrode surface followed by electrostripping and the charge measured. This experiment was repeated using various levels of NT-proBNP and the results obtained may been seen in FIG. 7, which shows charge vs. concentration in pg/ml, the pg/ml concentration being the final concentration, not the concentration of the solution added.

In this and the following examples, the working electrode area is 0.8 mm×4 mm=3.2 mm$^2$ and the charge was obtained by integrating under the peak from approximately −0.4 to 0.0 V after the background was removed (due to charging currents, any interferents etc). Potentials (in V) may be quoted as vs. (Carbon/$K_4Fe(CN)_6$, $K_3Fe(CN)_6$, $NH_4SCN$).

In more detail, silver sol conjugate was made by British Biocell international using an anti-NT-proBNP antibody and 80 nM diameter silver particles (OD 10). Magnetic particle conjugates were made by using latex covered paramagnetic particles (1.5 Mm diameter) with Hytest 15F11 anti-NT-proBNP antibody absorbed onto the surface and blocked with BSA to create a 10% solids solution.

The assay was performed by incubating silver sol conjugate (10 μl), magnetic particle conjugates (5 μl) and a spiked sample of NT pro-BNP (5 μl) for 5 minutes. The sample was then concentrated under a magnetic field and the supernatant removed. The sample was re-suspended in PBS (10 μl) concentrated by a bar magnet and the supernatant removed. This process was repeated one more time and then the particles were re-suspended and placed onto the electrode surface. All the magnetic particles were then moved over the working electrode. The dissolving solution of 0.106 g of $K_4Fe(CN)_6$ in 1 ml of 4M SCN was added (5 μl) to the electrode. The electrochemical measurement was performed on an autolab potentiostat, three screen printed carbon electrodes were used as working, counter and reference electrodes respectively, substantially as described in Example 1. The carbon ink used was D2 carbon ink from Gwent Electronic Materials.

The parameters for electrochemical analysis by anodic stripping voltammetry of silver were as follows:
1. 10 seconds at 0.35V to convert $Fe^{2+}$ to $Fe^{3+}$
2. 5 seconds at −1.6V
3. 55 seconds at −1.2V
4. Scan from −1.2V to 0.1V at a scan rate of 1 V s$^{-1}$ In step 1, ferricyanide is generated by oxidising ferrocyanide at the working electrode. Ferricyanide oxidises the silver causing it to dissolve. In steps 2 and 3, the silver is plated onto the electrode, and in step 4 the silver is stripped from the electrode. The stripping charge, Q, is extracted by integrating the area under the stripping peak from approximately −0.4 to 0.0 V after a background was removed (due to charging currents, any interference, etc), FIG. 7 demonstrates a response of the stripping charge to increasing analyte concentration.

Example 4

Figure 8:
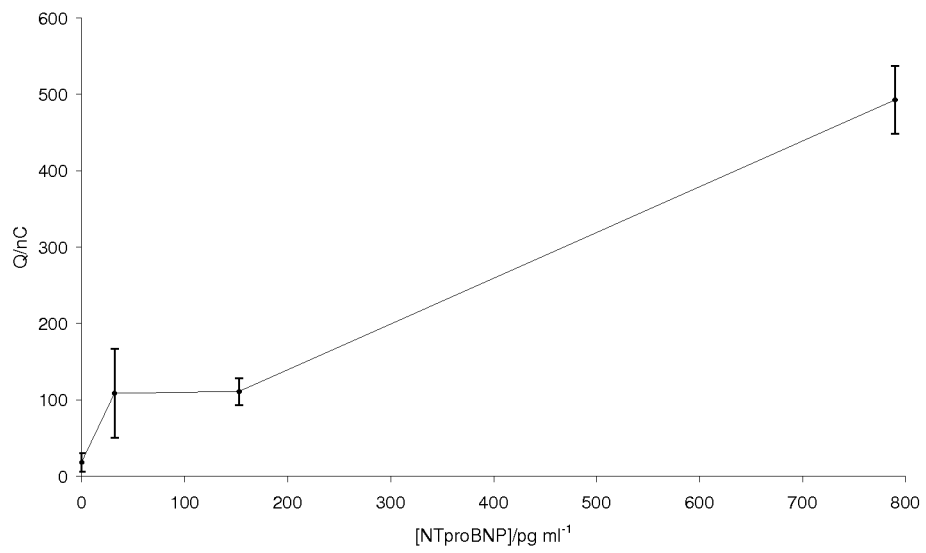
FIG. 8 is a graph of the amount of charge measured vs. the concentration of NT-proBNP added.

NTproBNP Immunoassay Based on the Trapping of 20 μm Diameter Latex Capture Particles with Silver Sol Signal Particles Using a Filter in a Channel In this example, latex-labelled NT-proBNP antibodies and Ag-labelled NT-proBNP antibodies were mixed with NT-proBNP. The resulting mixture was placed into a channel and flowed by capillary action to a filter region having a pore size of <=20 μm. The filter serves to capture the complex of latex-labelled antibody-analyte-Ag-labelled antibody (as well as any unbound latex antibody). Any unbound Ag-labelled antibody passes through the filter. Washing of the captured species was then carried out to remove any residual unbound Ag-labelled antibody and ferrocyanide solution was added. Both oxidation of the reagent and detection of silver ions was carried out by way of electrodes provided in the vicinity and upstream from the filter region. Thus, anti NT pro-BNP 20 μm latex capture particle conjugates were utilised to trap silver sol anti-NT pro-BNP conjugate which had NT pro-BNP captured on it. The latex particles were captured against a filter located next to an electrode in a channel and unbound silver conjugate material was washed away by passing solution through the packed bed of captured particles. Bound silver particles were measured by dissolution and subsequent stripping voltammetry at the electrode. This experiment was repeated several times and the amount of charge (corresponding to the amount of Ag ions detected by the electrode) was measured. FIG. 8 shows a plot of the amount of charge measured vs. the concentration of NT-proBNP added.

Figure 9:
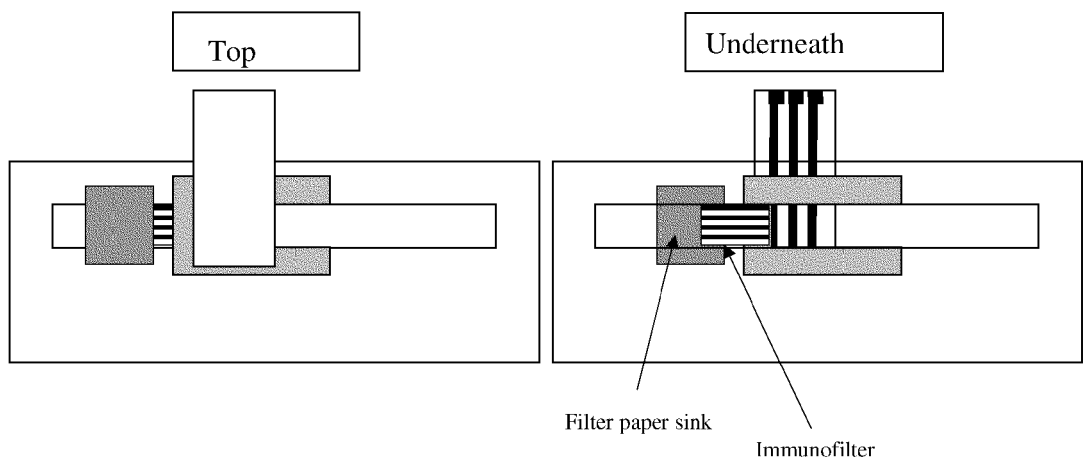
FIG. 9 is a diagrammatic representation of a microfluidic device used in Example 5.

In more detail, the device (see FIG. 9) consisted of a working, counter and reference electrode of D2 carbon ink from Gwent Electronic Materials screen printed onto mylar. This was attached using a U-shaped piece of double sided adhesive tape to a polystyrene moulded part, which was treated to make it hydrophilic, featuring a straight channel 50 μm deep and a filter. The working electrode (WE) is the leftmost electrode next to the filter. Sample was added to the right hand part of the channel in order to conduct the test. The channel width used was 4 mm. The dimensions of the filter are as follows: 5 mm long, 4 mm wide, channel width of 30 um and width of walls is 50 um. Number of channels (openings) in the filter is 49.

Solutions were prepared as follows. An NTproBNP standard ($1.953 \times 10^6$ pg ml$^{-1}$) in PBSA (Phosphate buffered saline with 0.05% azide) was diluted in 40 mg ml$^{-1}$ BSA to generate other standards.

In a 1.5 ml eppendorf was added 176 μl PBSA with 40 mg ml$^{-1}$ BSA and 30 μl of standard. This was mixed and to it was added 40 μl of Ag sol (the sol was made by British Biocell international using an anti-NTproBNP antibody and 80 nM silver particles and was blocked with β-casein and suspended in 0.5 mg ml$^{-1}$ β-casein in 10 mM borate, pH 8.5) with further mixing for 60 s. To this was added 33 μl latex at nominally 5% solids (20 μm diameter, sensitised with 15F11 antibody in PBSA) and the solution was mixed for 3 minutes.

The devices were filled by adding 0.5% Tween 20 solution followed by packing the bead bed with the latex, NTproBNP standard, silver sol solution. Washing was done with 15 μl PBSA to remove unbound silver and a further 5 μl was added to keep the capillary full. The packed bed was examined visually to estimate the covered electrode area. The capillary was sucked dry with gel blot, although liquid remained in the packed bead bed. Just before measuring electrochemically, 2.5 μl of 0.8 M SCN and 50 mM Ferrocyanide in PBSA was added to the bead bed.

For the electrochemical measurement:
1. Precondition for 5 s at 0 v
2. bias at 0.5 V for 40 s
3. hold at −1.0 V for 60 s
4. scan the potential from −1.0 V at scan rate of 0.5 V s$^{-1}$ to an end potential of 0.5 V.

In step 2, ferricyanide is generated by oxidising ferrocyanide at the working electrode, causing silver sol to be oxidised and dissolve. In step 3 the silver is plated onto the electrode, and in step 4 the silver is stripped from the electrode. The stripping charge, Q, is extracted by integrating the area under the stripping peak after a background is subtracted.

The results can be seen in FIG. 8, which is a plot of measured charge vs. concentration of NTproBNP on a log scale. Error bars represent one standard deviation in the measured signal based on 3 or 4 measurements. FIG. 8 demonstrates a response of the stripping charge to increasing analyte concentration.

Example 5

Use of Iodoacetamide in Measurement of Silver in Plasma

This example shows the effect of adding iodoacetamide. A potential problem with using Ag in the presence of solutions that contain protein, such as blood or plasma, is that Ag binds strongly to proteins through thiol groups and becomes electrochemically inactive or its activity is electrochemically reduced. Therefore, iodoacetamide, which also binds strongly to proteins, was added to act as a protein sequestering agent, thus removing the ability of the proteins to bind Ag. This reagent can be provided in the dry state within a device.

The basis for using iodoacetamide is its reaction with thiols found in proteins to form thioesters. Iodoacetamide has the following structure and reaction with thiols:

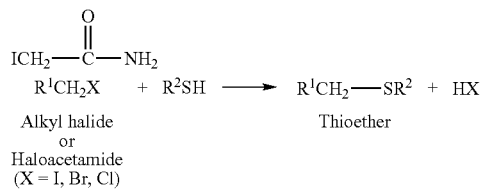

Iodoacetamide was added to a plasma sample at 80% concentration from a stock solution of 500 mM in methanol to give a concentration of 5 mM. 20 μl of the plasma (with or without iodoacetamide) was mixed with 5 μl of 4 M NH$_4$SCN, 250 mM potassium ferricyanide and 25 mM potassium ferrocyanide, with various concentrations of AgNO$_3$. The resulting solution, containing 4 mM iodoacetamide, 0.8 M NH$_4$SCN, 50 mM potassium ferricyanide and 5 mM potassium ferrocyanide, with various concentrations of AgNO$_3$ was applied to the electrode. The potential was scanned to −1.6V at 1V/s, kept at −1.6V for 5 s, and subsequently stepped to −1.2V and kept there for 115 s. Subsequently, the potential was scanned to 0.1 V by 1V/s. The stripping charge, Q, is extracted by integrating the area under the stripping peak after a background is subtracted.

Figure 10:
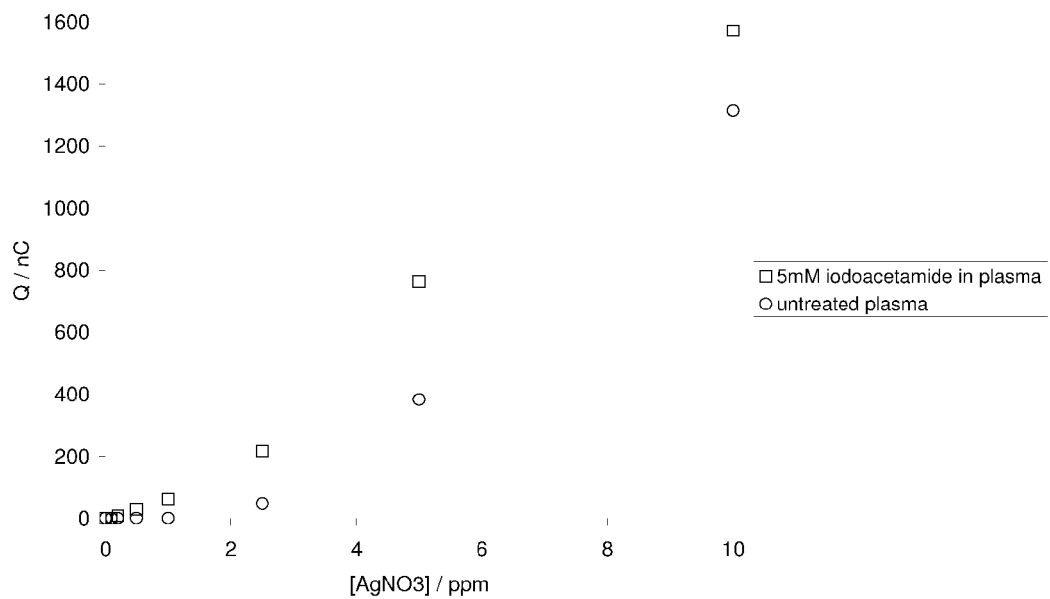
FIG. 10 is a graph illustrating the measurement of silver ions in a plasma sample in the presence or absence of 5 mM iodoacetamide.

The results are shown in FIG. 10. It can be seen that, in the absence of iodoacetamide, the signal for silver at low levels is very small. Adding iodoacetamide recovers some of the silver signal, allowing detection of silver at much lower levels.

We claim:

1. A method for determining the presence or amount of a silver-labelled species in a sample, the method comprising:
    applying the sample to a test device in a dry state, the test device comprising dried reagents;
    causing the metal of the silver-labelled species in the sample to form a soluble electrochemically-active complex which is stable relative to moieties present or potentially present in the sample which moieties will form an insoluble and/or electrochemically-inactive complex with the silver, wherein the electrochemically-active complex is formed by oxidising the silver to form a silver ion and reacting the silver ion with a complexing agent according to the following reaction: $Ag^+ + m(NH_4)^+ + n(SCN)^- \rightarrow [Ag(NH_4)^+_m(SCN^-)_n]^{m-n+1}$; and
    electrochemically measuring the formed complex to provide an indication of the presence or amount of the silver-labelled species.

2. A method as claimed in claim 1, wherein the metal label is particulate.

3. A method as claimed in claim 1, wherein measurement of the electrochemically active complex is carried out by anodic stripping voltammetry.

4. A method as claimed in claim 1, wherein the metal-labelled species is formed by the binding of an analyte to be detected with a metal-labelled binding partner.

5. A method as claimed in claim 1, wherein the metal-labelled binding partner is an antibody or antigen binding fragment thereof.

6. A method as claimed in claim 1, wherein the sample is a biological sample.

* * * * *